(12) United States Patent
Tanaka et al.

(10) Patent No.: US 7,732,573 B2
(45) Date of Patent: Jun. 8, 2010

(54) METHOD FOR PRODUCING POROUS BODY COMPRISING APATITE/COLLAGEN COMPOSITE FIBERS

(75) Inventors: Junzo Tanaka, Ibaraki-ken (JP); Masanori Kikuchi, Ibaraki-ken (JP); Toshiyuki Ikoma, Ibaraki-ken (JP); Daisuke Shoji, Tokyo (JP); Katsumi Kawamura, Tokyo (JP); Takehiko Nakajima, Saitama (JP); Naomi Mochizuki, Tokyo (JP)

(73) Assignees: National Institute for Materials Science, Ibaraki-ken (KP); Hoya Corporation, Tokyo (JP)

( * ) Notice: Subject to any disclaimer, the term of this patent is extended or adjusted under 35 U.S.C. 154(b) by 423 days.

(21) Appl. No.: 11/718,135

(22) PCT Filed: Oct. 13, 2005

(86) PCT No.: PCT/JP2005/018891

§ 371 (c)(1),
(2), (4) Date: Apr. 27, 2007

(87) PCT Pub. No.: WO2006/046414

PCT Pub. Date: May 4, 2006

(65) Prior Publication Data

US 2009/0166580 A1 Jul. 2, 2009

(30) Foreign Application Priority Data

Oct. 28, 2004 (JP) ............................. 2004-314343

(51) Int. Cl.
| *A61K 38/17* | (2006.01) |
| *A61F 2/02* | (2006.01) |
| *A61F 2/28* | (2006.01) |
| *A61L 27/32* | (2006.01) |
| *D04H 1/54* | (2006.01) |
| *D04H 1/00* | (2006.01) |
| *C03B 37/00* | (2006.01) |
| *B29C 65/00* | (2006.01) |

(52) U.S. Cl. ................. 530/356; 623/11.11; 623/16.11; 623/23.51; 623/23.61; 623/23.56; 427/2.27; 442/411; 442/414; 162/3; 156/296

(58) Field of Classification Search ............ 252/182.12; 521/64; 428/189; 530/356; 623/11.11, 16.11, 623/23.51, 23.61, 23.56; 442/411, 414; 162/3; 427/2.27; 156/296
See application file for complete search history.

(56) References Cited

U.S. PATENT DOCUMENTS

| 5,776,193 | A | 7/1998 | Kwan et al. |
| 7,153,938 | B2 | 12/2006 | Kikuchi et al. |
| 7,163,965 | B2 * | 1/2007 | Sotome et al. ................. 521/64 |
| 2005/0255779 | A1 * | 11/2005 | Mizutani et al. ............ 442/411 |
| 2006/0292350 | A1 | 12/2006 | Kawamura et al. |
| 2007/0282455 | A1 * | 12/2007 | Luginbuehl et al. ...... 623/23.72 |

FOREIGN PATENT DOCUMENTS

| JP | 11-513590 | 11/1999 |
| JP | 2005-279078 | 10/2005 |
| WO | 97/14376 | 4/1997 |
| WO | 03/035128 | 5/2003 |
| WO | 03/047645 | 6/2003 |
| WO | 03/092759 | 11/2003 |
| WO | 2004/041320 | 5/2004 |
| WO | 2004/103422 | 12/2004 |

OTHER PUBLICATIONS

Kikuchi et al., "Porous Body Preparation of Hydroxyapatite/Collagen Nanocomposites for Bone Tissue Regeneration," Key Engineering Materials, vols. 254-256, pp. 561-564 (2004).
English Language abstract of JP 2005-279078.
Gelinski, M, et al., "Porous Scaffolds made from Mineralized Collagen—a Biomimetic Bone Graft Material", Mat.-wiss. U. Werkstofftech., vol. 35, No. 4, pp. 229-233 (2004).
U.S. Appl. No. 10/599,435, filed Sep. 28, 2006.

* cited by examiner

*Primary Examiner*—Ling-Siu Choi
*Assistant Examiner*—Monique Peets
(74) *Attorney, Agent, or Firm*—Greenblum & Bernstein; P.L.C.

(57) ABSTRACT

A method for producing a porous body comprising apatite/collagen composite fibers comprising the steps of gelling a dispersion comprising long apatite/collagen composite fibers having an average length of 10-75 mm, short apatite/collagen composite fibers having an average length of 0.05-1 mm, and a liquid; freezing and drying the resultant gel to form a porous body; and cross-linking collagen in the porous body.

4 Claims, 7 Drawing Sheets

750 μm

750 μm

750 µm

750 µm

US 7,732,573 B2

METHOD FOR PRODUCING POROUS BODY COMPRISING APATITE/COLLAGEN COMPOSITE FIBERS

FIELD OF THE INVENTION

The present invention relates to a method for producing a porous body comprising an apatite/collagen composite fibers (hereinafter referred to simply as "apatite/collagen porous body") suitable for artificial bone, cell scaffolds, etc., particularly to a method for producing an apatite/collagen porous body without using a binder such as collagen, etc.

BACKGROUND OF THE INVENTION

Because of excellent compatibility with human bone, artificial bone made of apatite can be bonded to the human bone directly. Accordingly, the artificial bone made of apatite has recently been appreciated for effectiveness, finding clinical applications in cosmetic surgery, neurosurgery, plastic surgery, oral surgery, etc. However, artificial ceramic bone such as apatite is not necessarily completely identical with human bone in terms of mechanical properties and physiological properties. For instance, a so-called artificial ceramic bone made only of apatite is harder and more brittle than the human bone. While the human bone is repeatedly subjected to metabolism of absorption and regeneration, the artificial bone made of apatite is not substantially dissolved but semi-permanently remains in the human body. The remaining artificial bone breaks the human bone at their interface, making it likely to cause bone fracture.

Research has recently become active on artificial bone decomposable in the human body, which is closer in composition to human bone than the artificial apatite bone, and various proposals have been made. For instance, JP 11-513590 A discloses a porous body having a network structure, in which collagen and, if necessary, other binders are bonded to hydroxyapatite. Human bone is formed in the porous body, and the porous body is biologically decomposed and absorbed by the human body. Accordingly, this porous body can be used for the fixation of vertebra, the filling of bone defects, the repair of fractured bone, the grafting of periodontal defects, etc. However, this porous body is a mere mixture of collagen and apatite, which does not have a similar structure to the living bone, namely a structure in which the C-axis of apatite is oriented along collagen fibers. Further, it does not have sufficient mechanical strength, and is poor in bone-forming capability.

To solve this problem, the inventors previously disclosed a porous body that can be absorbed by the body according to a similar mechanism to the living bone, and has high bone-forming capability (WO 2004/041320 A1). This porous body is obtained by freeze-drying a dispersion comprising an apatite/collagen composite and collagen to form a porous body, and cross-linking collagen in the porous body. When the apatite/collagen composite contained in the porous body embedded in a living body is dissolved and/or decomposed, it is considered that there appears an environment suitable for forming bone in and around the porous body. The dissolved and/or decomposed apatite/collagen composite is absorbed by a newly formed living bone. However, further research by the inventors has revealed that the apatite/collagen composite is covered with collagen, a binder, in this method. As a result, some part of the apatite/collagen composite does not appear on the porous body surface, so that the porous body is not well absorbed in the course of regeneration of the living bone.

OBJECT OF THE INVENTION

Accordingly, an object of the present invention is to provide a method for producing an apatite/collagen porous body having high bone-forming capability without using a binder such as collagen, etc.

DISCLOSURE OF THE INVENTION

As a result of intense research in view of the above object, the inventors have found that when a mixture comprising long fibers and short fibers both composed of an apatite/collagen composite is used as a starting material, an apatite/collagen porous body having excellent bone-forming capability can be obtained without using a binder. The present invention has been completed based on this finding.

Thus, the method of the present invention for producing an apatite/collagen porous body comprises the steps of gelling a dispersion comprising long apatite/collagen composite fibers having an average length of 10-75 mm, short apatite/collagen composite fibers having an average length of 0.05-1 mm, and a liquid such as water; freezing and drying the resultant gel to form a porous body; and cross-linking collagen in the porous body.

A binder such as collagen, etc. is preferably not added to the dispersion. The ratio of the long fibers to the short fibers is preferably 0.2-0.8 in the dispersion.

DESCRIPTION OF THE BEST MODE OF THE INVENTION

Figure 1:
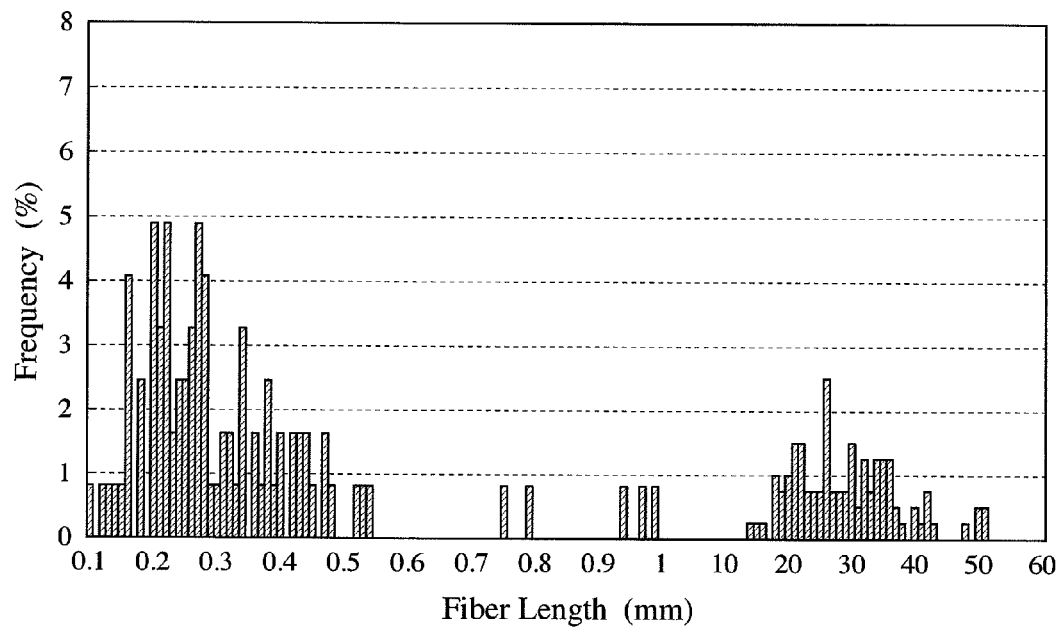
FIG. 1 is a graph showing the length distribution of apatite/collagen composite fibers contained in the porous body of Example 1.

[1] Production of Long Apatite/Collagen Composite Fibers and Short Apatite/Collagen Composite Fibers (1) Starting Materials Long apatite/collagen composite fibers and short apatite/collagen composite fibers (hereinafter referred to simply as "apatite/collagen composite fibers") are produced from collagen, phosphonic acid or its salts, and calcium salts, as starting materials. Though not particularly restricted, the collagen may be extracted from animals, etc. The kinds, parts, ages, etc. of the animals are not particularly restrictive. In general, collagen obtained from skins, bones, cartilages, tendons, internal organs, etc. of mammals such as cow, pig, horse, rabbit and rat, and birds such as hen, etc. may be used. Collagen-like proteins obtained from skins, bones, cartilages, fins, scales, internal organs, etc. of fish such as cod, flounder, flatfish, salmon, trout, tuna, mackerel, red snapper, sardine, shark, etc. may also be used. The extraction method of collagen is not particularly restrictive but may be a usual one. In place of collagen extracted from animal tissues, collagen produced by gene recombination technologies may also be used.

Phosphoric acid or its salts [hereinafter referred to simply as "phosphoric acid (salt)"] include phosphoric acid, disodium hydrogenphosphate, sodium dihydrogenphosphate, dipotassium hydrogenphosphate, potassium dihydrogenphosphate, etc. The calcium salts include calcium carbonate, calcium acetate, and calcium hydroxide, etc. The phosphate and the calcium salt are preferably added in the form of a uniform aqueous solution or suspension.

An apatite/collagen mass ratio in the product can be controlled by a mass ratio of the apatite-forming materials [phosphoric acid (salt) and calcium salt] and collagen used. Accordingly, the mass ratio of the apatite-forming materials and collagen used is properly determined depending on a targeted composition ratio of the apatite/collagen composite fibers. A ratio of apatite to collagen in the apatite/collagen composite fibers is preferably 9/1 to 6/4, for instance, 8/2. The apatite/collagen ratio may be the same or different between the long fibers and the short fibers.

(2) Preparation of Solution

First, an aqueous phosphoric acid (salt) solution and an aqueous calcium salt solution are prepared. The concentrations of an aqueous phosphoric acid (salt) solution and an aqueous calcium salt solution affect the length of fibers formed. Specifically, the higher the concentrations of the aqueous phosphoric acid (salt) solution and/or the aqueous calcium salt solution, the shorter the resultant apatite/collagen composite fibers. Accordingly, their concentrations should be decided depending on the length of fibers to be formed. Also, in the later-described dropping step, the concentrations of solutions such as the aqueous phosphoric acid (salt) solution and the aqueous calcium salt solution should be decided to avoid them from becoming out of balance.

To produce fibers (long apatite/collagen composite fibers) having an average fiber length of 10-75 mm, the aqueous phosphoric acid (salt) solution preferably has a concentration of about 10-50 mM, and the aqueous calcium salt solution preferably has a concentration of about 50-200 mM. When the concentration of the aqueous phosphoric acid (salt) solution is higher than 50 mM, or when the concentration of the aqueous calcium salt solution is higher than 200 mM, the formed fibers tend to have an average length of less than 10 mm. When the concentration of the aqueous phosphoric acid (salt) solution is less than 10 mM, or when the concentration of the aqueous calcium salt solution is less than 50 mM, the average fiber length tends to be more than 75 mm. 90% by mass or more of the long apatite/collagen composite fibers are as long as 5-100 mm.

To produce fibers (short apatite/collagen composite fibers) having an average fiber length of 0.05-1 mm, the concentration of the aqueous phosphoric acid (salt) solution is preferably about 50-250 mM, and the concentration of the aqueous calcium salt solution is preferably about 200-600 mM. When the concentration of the aqueous phosphoric acid (salt) solution is higher than 250 mM, or when the concentration of the aqueous calcium salt solution is higher than 600 mM, the average fiber length tends to be less than 0.05 mm. When the concentration of the aqueous phosphoric acid (salt) solution is less than 50 mM, or when the concentration of the aqueous calcium salt solution is less than 200 mM, the average fiber length tends to be more than 1 mm. 90% by mass or more of the short apatite/collagen composite fibers are as long as 0.01-2 mm.

The collagen generally in the form of an aqueous phosphoric acid solution is added to the above-described aqueous phosphoric acid (salt) solution. In the aqueous solution of collagen in phosphoric acid, the concentration of the collagen is about 0.5-1% by mass, while the concentration of the phosphoric acid is about 10-30 mM. Practically, the concentration of the collagen is 0.8-0.9% by mass, for instance, 0.85% by mass, and the concentration of phosphoric acid is about 15-25 mM, for instance, 20 mM.

(3) Mixing of Aqueous Phosphoric Acid (Salt) Solution with Aqueous Calcium Salt Solution With water about ½-2 times the aqueous calcium salt solution charged into a reactor in advance, an aqueous phosphoric acid (salt) solution containing the collagen and the aqueous calcium salt solution are simultaneously dropped into the reactor. The dropping speed is preferably about 10-50 ml/min while stirring the reaction solution at about 50-300 rpm. During the dropping, it is preferable to keep the concentrations of calcium and phosphoric acid ions in the reaction solution to 3.75 mM or less and 2.25 mM or less, respectively, to keep the reaction solution at pH of 8.9-9.1. Outside the above concentration ranges of calcium and/or phosphoric acid ions, the self-organization of the composite is hindered. The term "self-organization" used herein means that hydroxyapatite (calcium phosphate having an apatite structure) has orientation peculiar to living bone along collagen fibers, namely that the C-axis of the hydroxyapatite is in alignment with the collagen fibers. Under the above dropping conditions, the apatite/collagen composite fibers are self-organized. Each of the long apatite/collagen composite fibers and the short apatite/collagen composite fibers is provided with an average length in a predetermined range.

After the completion of dropping, a slurry-like mixture of the apatite/collagen composite fibers and water is freeze-dried. The freeze-drying can be carried out by rapid drying in vacuum in a frozen state at −10° C. or lower.

[2] Preparation of Dispersion Containing Long Apatite/Collagen Composite Fibers and Short Apatite/Collagen Composite Fibers The long apatite/collagen composite fibers and the short apatite/collagen composite fibers are preferably mixed with each other at a long fibers/short fibers mass ratio of 0.2-0.8. When the mass ratio of long fibers to short fibers is less than 0.2, it is difficult to provide the apatite/collagen porous body with sufficient mechanical strength. When the mass ratio of long fibers to short fibers is more than 0.8, enough effect of dispersing the short fibers cannot be obtained, so that the fibers are easily separated from water.

A mixture of the long apatite/collagen composite fibers and the short apatite/collagen composite fibers (hereinafter referred to simply as "apatite/collagen composite fiber mixture") is stirred with a liquid such as water, an aqueous phosphoric acid solution, etc. to prepare a paste-like dispersion. The liquid used for preparing the dispersion should be able to well disperse the apatite/collagen composite fibers. Preferred examples of the dispersant include water, a phosphoric acid buffer solution (PBS), and a physiological saline solution. The addition of PBS to the dispersion provides good dispersing effect to the apatite/collagen composite fiber mixture, and increases the ion strength of the dispersion, thereby accelerating the gelation.

The amount of the liquid is determined such that the percentage of the liquid in the dispersion containing the apatite/collagen composite fibers is preferably 80 to 99% by volume, more preferably 90 to 97% by volume. The resultant porous body has porosity P, which depends on a volume ratio of the apatite/collagen composite fibers to the liquid in the dispersion as represented by the following formula (1):

$$P = Y/(X+Y) \times 100 \quad (1),$$

wherein X represents the volume of the apatite/collagen composite fibers in the dispersion, and Y represents the volume of the liquid in the dispersion. Accordingly, it is possible to control the porosity P of the porous body by adjusting the amount of the liquid to be added. Incidentally, the volume Y of a liquid in the dispersion includes the volume of the later-described phosphoric acid buffer solution (PBS).

[3] Gelation of Dispersion

When a liquid (water, physiological saline solution, etc.) other than PBS is used in the step of preparing the above dispersion, the phosphoric acid buffer solution (PBS) as concentrated as about 2.5-10 times is added to the dispersion and stirred to adjust its ion strength to 0.2-0.8. The more preferred ion strength is at the same level as that of PBS. The larger ion strength of the dispersion accelerates the gelation of the dispersion. When PBS is used in the preparation of the dispersion, PBS need not be added at this stage.

The dispersion charged into a molding die is kept at a temperature of 35° C. to 43° C. for gelation. For sufficient gelation of the dispersion, the heating time is preferably 0.5 to 3.5 hours, more preferably 1 to 3 hours. With the dispersion kept at a temperature of 35-43° C., the gelation of the dispersion can be accelerated. The gelled dispersion can prevent the apatite/collagen composite fibers from precipitating therein, thereby producing a uniform porous body. The gelation treatment provides a jelly-like product comprising the apatite/collagen composite fibers uniformly dispersed in the liquid.

Figure 2:
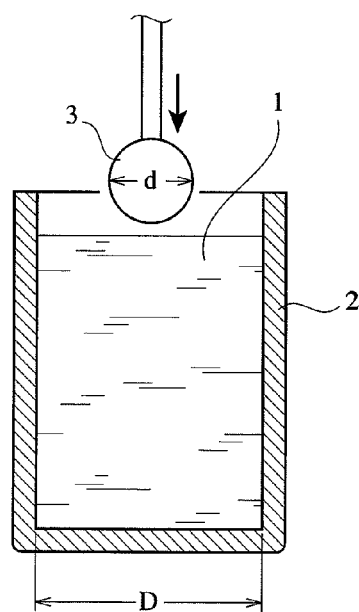
FIG. 2 is a cross-sectional view showing an apparatus for measuring the gel strength.

Using the apparatus shown in FIG. 2, the strength of a gel molding can be measured. The gel molding 1 held in a cylindrical mold 2 is pushed from above by a ball 3. When the ratio of the diameter d of the ball 3 to the diameter D of the gel molding is about 0.2-0.8, stress generated when the molding 1 is compressed 5 mm by the ball 3 is preferably 0.1-0.5 N. When the strength of the gel molding is less than 0.1 N, the gel molding is easily broken, resulting in difficult operation. The gel molding generating larger stress than 0.5 N excessively contains the apatite/collagen composite fiber mixture per a unit volume, forming a porous body with too small porosity.

[4] Freeze-Drying of Gel

The gel containing the apatite/collagen composite fibers is frozen in a freezer. The average pore diameter of the resultant apatite/collagen porous body depends on the gel-freezing time. The temperature in the freezer is preferably −100° C. to 0° C., more preferably −100° C. to −10° C., particularly −80° C. to −20° C. When it is lower than −100° C., the resultant apatite/collagen porous body has too small an average pore diameter. When it is higher than 0° C., the gel is not frozen, or freezing takes too much time, resulting in a porous body with too large an average pore diameter.

The solidified gel is freeze-dried to a porous body. The freeze-drying is conducted by evacuating the frozen gel at −10° C. or lower, and rapidly drying it, as in the case of the apatite/collagen composite fibers. The freeze-drying need only be conducted until the dispersion is fully dried, so the freezing time is not particularly restricted, but it is generally about 24-72 hours.

[5] Cross-Linking of Collagen

The cross-linking of collagen may be carried out by any methods such as physical cross-linking methods using γ-rays, ultraviolet rays, thermal dehydration, electron beams, etc., or chemical cross-linking methods using cross-linking agents, condensation agents, etc. In the case of the chemical cross-linking, the freeze-dried porous body is immersed in a cross-linking agent solution to cross-link collagen in the porous body. The cross-linking agents may be, for instance, aldehydes such as glutaraldehyde, formaldehyde, etc.; isocyanates such as hexamethylene diisocyanate, etc.; carbodiimides such as a hydrochloric acid salt of 1-ethyl-3-(3-dimethylaminopropyl)carbodiimide; polyepoxides such as ethylene glycol diethyl ether, etc.; transglutaminase, etc. Among these cross-linking agents, glutaraldehyde is particularly preferable from the aspects of the easiness of controlling the degree of cross-linking and the biocompatibility of the resultant porous body.

When cross-linking is conducted by using glutaraldehyde, the concentration of a glutaraldehyde solution is preferably 0.005 to 0.015% by mass, more preferably 0.005 to 0.01% by mass. The porous body should be dehydrated. When alcohol such as ethanol, etc. is used as a solvent for the glutaraldehyde solution, the dehydration of the porous body and the cross-linking of collagen may be conducted in a single step. Dehydration and cross-linking in a single step cause the cross-linking reaction of collagen in a state where the apatite/collagen composite fibers are contracted, resulting in a porous body with improved elasticity.

After the cross-linking, the porous body is immersed in an aqueous solution of about 2% by mass of glycine to remove unreacted glutaraldehyde, and then washed with water. The porous body is further immersed in ethanol for dehydration, and then dried at room temperature.

In the case of cross-linking during thermal dehydration, the freeze-dried porous body may be kept at 100° C. to 160° C. and 0-100 hPa for 10-12 hours in a vacuum oven.

The present invention will be explained in more detail with reference to Examples below without intention of restricting the scope of the present invention.

EXAMPLE 1

(1) Production of Long Apatite/Collagen Composite Fibers 412 g of an aqueous solution of collagen in phosphoric acid (concentration: 0.97% by weight, phosphoric acid: 20 mM) was added to 400 g of a 30-mM aqueous phosphoric acid solution and stirred to prepare a solution a-1. 400 ml of a 100-mM calcium hydroxide solution (solution b-1) was also prepared. After 200 ml of water was charged into a reactor, the solutions a-1 and b-1 were simultaneously dropped, and the resultant reaction solution was stirred. With the pH of the reaction solution kept at 8.9-9.1 during dropping, formed slurry was frozen and freeze-dried.

Figure 3:
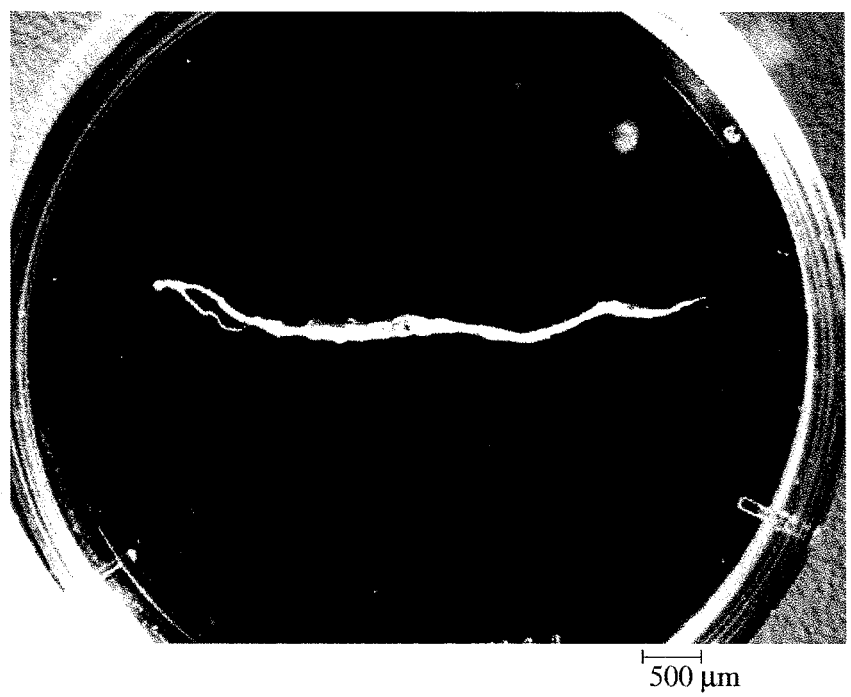
FIG. 3 is an optical photomicrograph of a long apatite/collagen composite fiber.

The resultant fibers had an average length of 65 mm. The optical photomicrograph of a long apatite/collagen composite fiber is shown in FIG. 3. An apatite/collagen ratio in the long apatite/collagen composite fibers was 8/2 by mass.

Figure 4:
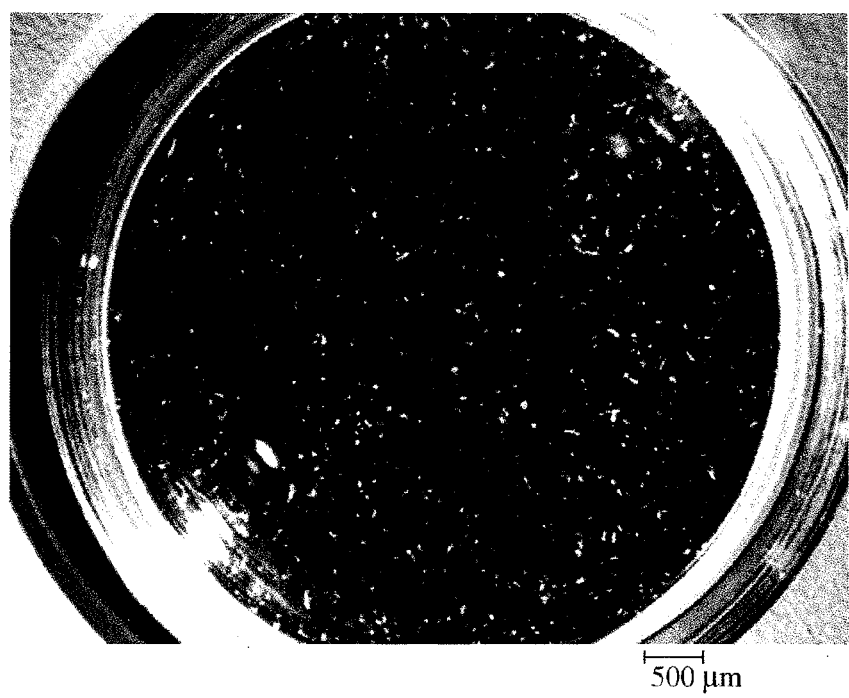
FIG. 4 is an optical photomicrograph of short apatite/collagen composite fibers.

(2) Production of Short Apatite/Collagen Composite Fibers 412 g of an aqueous solution of collagen in phosphoric acid (concentration: 0.97% by weight, phosphoric acid: 20 mM) was added to 400 g of a 120-mM aqueous phosphoric acid solution and stirred to prepare a solution a-2. 400 ml of a 400-mM calcium hydroxide solution (solution b-2) was also prepared. An apatite/collagen composite was produced in the same manner as in the step (1) in Example 1, except that the solutions a-2 and b-2 were dropped into water in the reactor. The resultant fibers had an average length of 0.23 mm. The optical photomicrograph of short apatite/collagen composite fibers is shown in FIG. 4. An apatite/collagen ratio in the short apatite/collagen composite fibers was 8/2 by mass.

(3) Production of Apatite/Collagen Porous Body

The long apatite/collagen composite fibers and the short apatite/collagen composite fibers were mixed at a mass ratio shown in Table 1. The fiber length distribution of the resultant apatite/collagen composite fiber mixture is shown in FIG. 1. 1 g of the apatite/collagen composite fiber mixture was then mixed with 7.87 ml of PBS and stirred to obtain a dispersion. The amount of a liquid (pure water, PBS) added was 95% by volume of the dispersion.

(4) Measurement of Strength of Gel Molding

Figure 5:
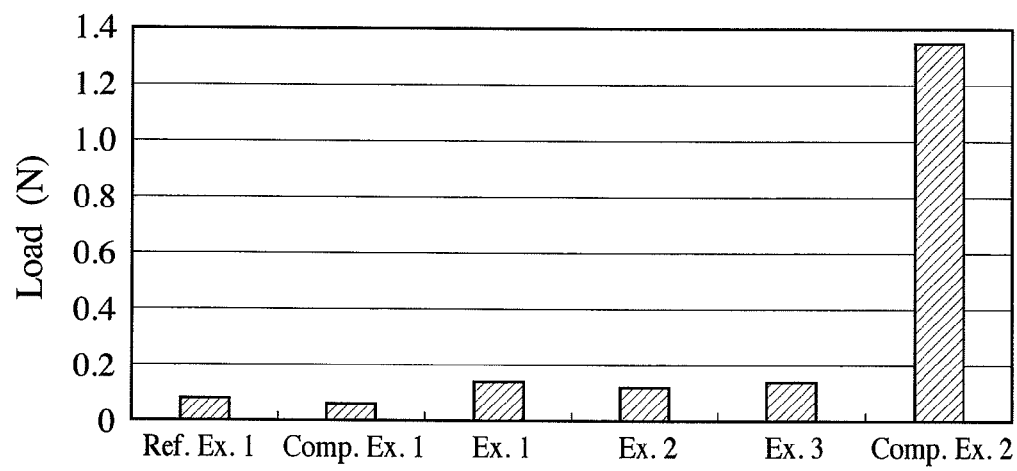
FIG. 5 is a graph showing the strength of a gel molding containing apatite/collagen composite fibers.

The dispersion containing the long apatite/collagen composite fibers and the short apatite/collagen composite fibers was charged into a polystyrene-made, cylindrical mold of 10 mm in inner diameter and 10 mm in height, and kept at 37° C. for 2 hours to form a gel molding. This gel molding 1 was pushed from above by a ball 3 of 7 mm in diameter as shown in FIG. 2, to measure a load (gel strength) necessary for compressing the gel molding 1 by 5 mm. The measurement results are shown in FIG. 5 and Table 2.

(5) Cross-Linking

Figure 6:
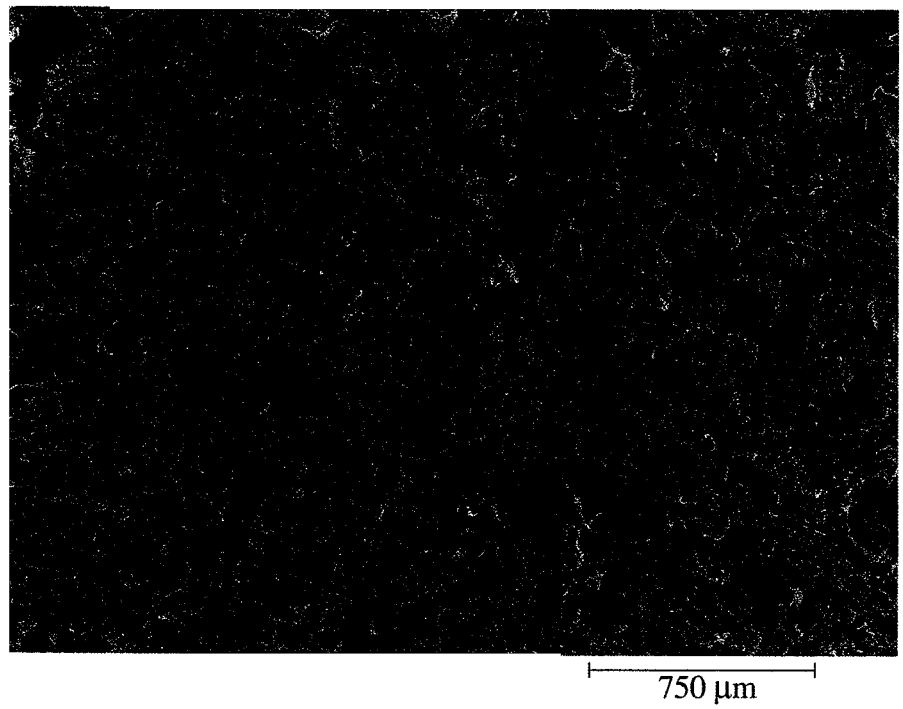
FIG. 6 is a scanning electron photomicrograph (SEM photograph) showing the apatite/collagen porous body of Example 1.

The gel molding was frozen in a freezer set at −80° C. The solidified body was dried in a vacuum oven (0° C. to 240° C., 760 Torr to 1 Torr), evacuated to 1.33 hPa, and cross-linked during thermal dehydration at 140° C., to obtain an apatite/collagen porous body. The scanning electron photomicrograph (SEM photograph) of a cross section of the porous body is shown in FIG. 6. It is clear from FIG. 6 that long fibers were entangled with short fibers to provide pores having uniform diameters in the porous body.

EXAMPLES 2 AND 3

Figure 7:
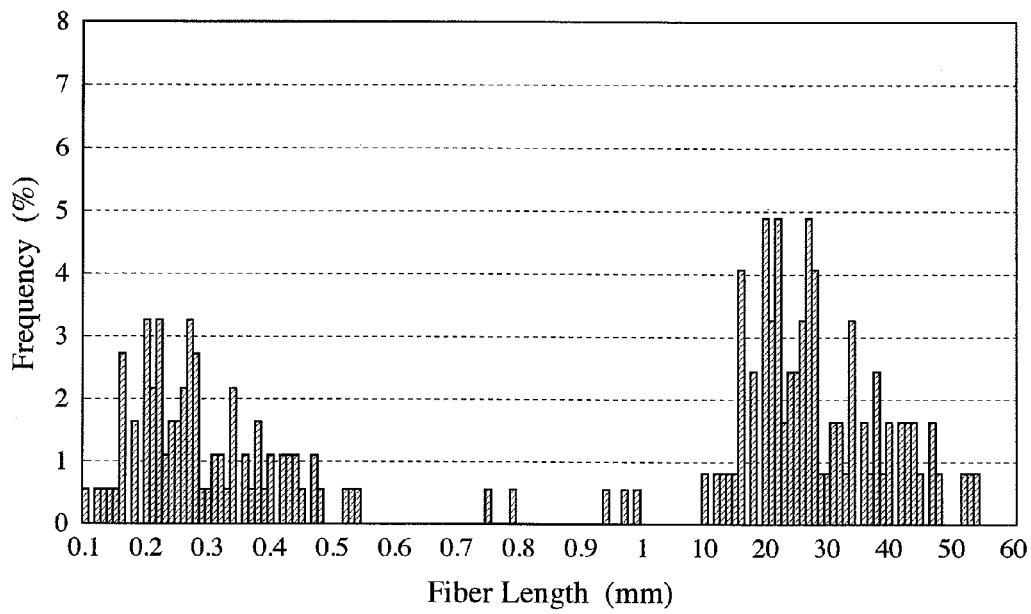
FIG. 7 is a graph showing the length distribution of apatite/collagen composite fibers contained in the porous body of Example 2.
Figure 8:
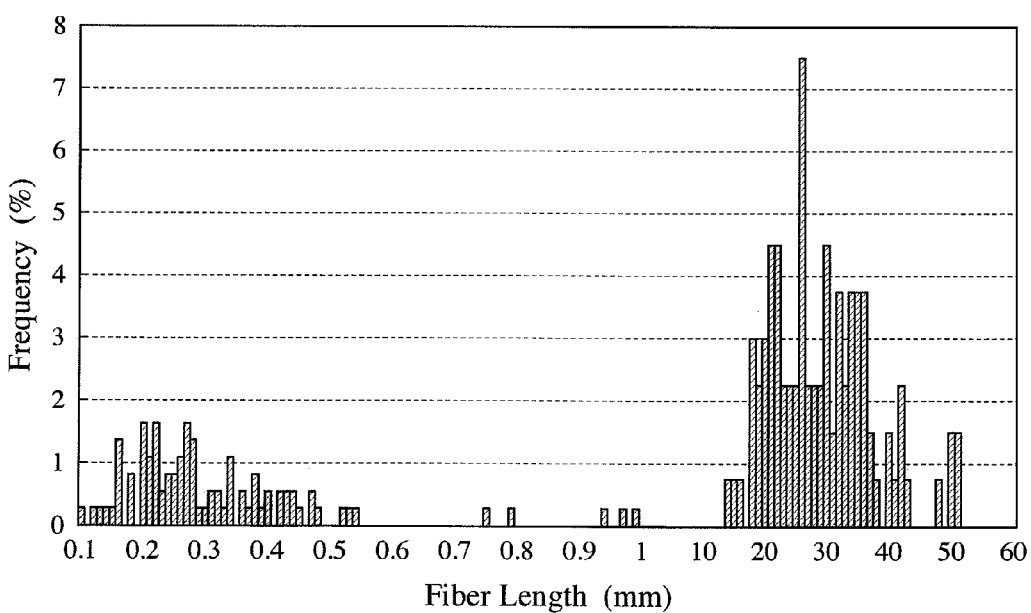
FIG. 8 is a graph showing the length distribution of apatite/collagen composite fibers contained in the porous body of Example 3.

Each gel molding was produced in the same manner as in the steps (1) to (4) in Example 1 except for changing the mixing ratio of the long apatite/collagen composite fibers to the short apatite/collagen composite fibers to those shown in the columns of Examples 2 and 3 in Table 1, and compressed from above by a ball to measure the gel strength. Their length distributions of the apatite/collagen composite fibers are shown in FIGS. 7 and 8, and their measured gel strengths are shown in FIG. 5 and Table 2.

Figure 9:
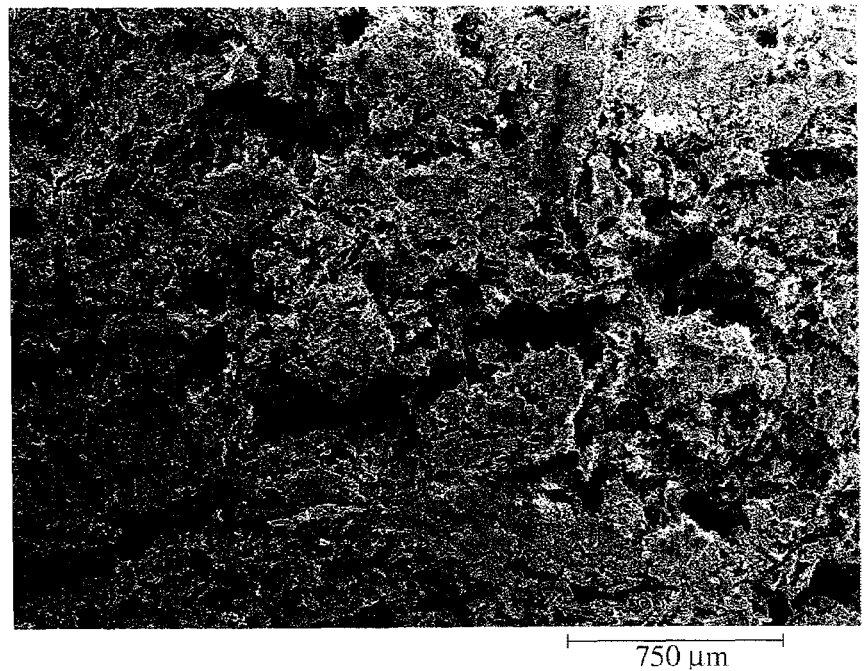
FIG. 9 is a scanning electron photomicrograph (SEM photograph) showing a cross section of the apatite/collagen porous body of Example 2.
Figure 10:
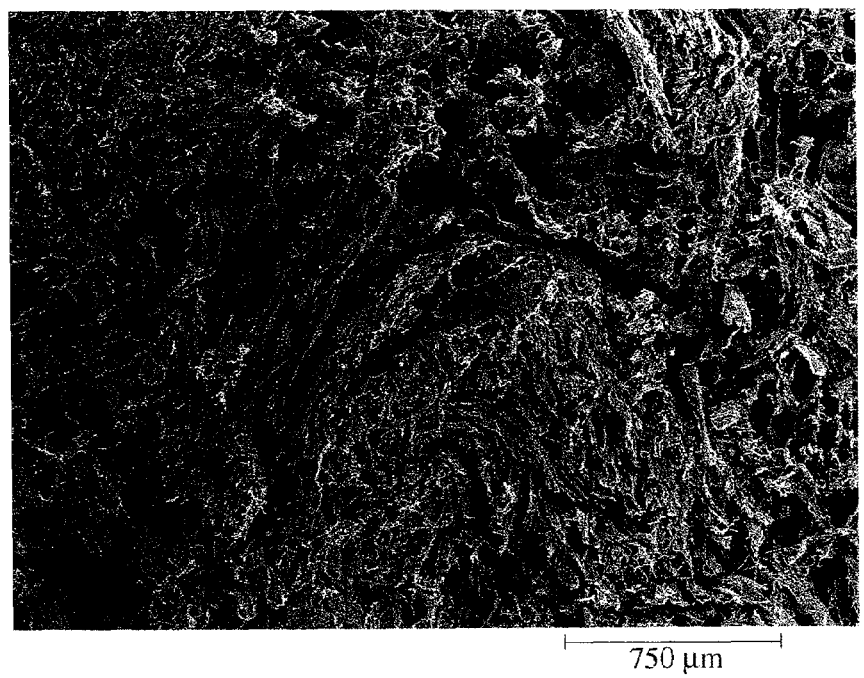
FIG. 10 is a scanning electron photomicrograph (SEM photograph) showing a cross section of the apatite/collagen porous body of Example 3.

Each gel molding was frozen and dried, and then cross-linked during thermal dehydration in the same manner as in the step (5) in Example 1, to obtain an apatite/collagen porous body. The scanning electron photomicrographs (SEM photographs) of the cross sections of the porous bodies are shown in FIGS. 9 and 10.

COMPARATIVE EXAMPLE 1

Figure 11:
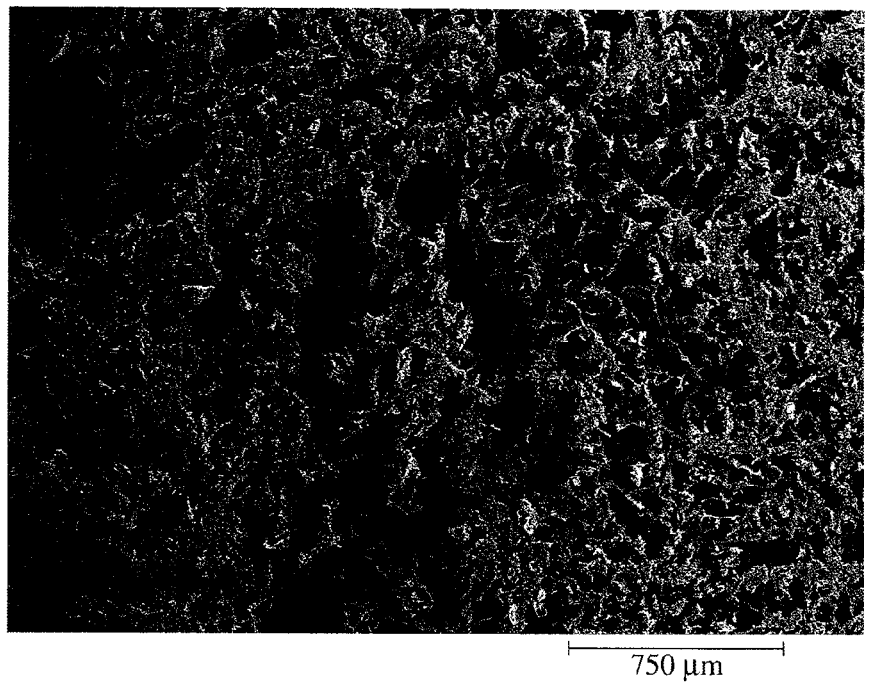
FIG. 11 is a scanning electron photomicrograph (SEM photograph) showing a cross section of the porous body of Comparative Example 1 comprising short apatite/collagen composite fibers.

A gel molding was produced in the same manner as in Examples 1-3, except that a dispersion containing short apatite/collagen composite fibers without long apatite/collagen composite fibers was prepared, compressed from above by a ball to measure the gel strength, and then subjected to the cross-linking of collagen. The measured gel strength is shown in FIG. 5 and Table 2. This gel molding did not have sufficient mechanical strength. The SEM photograph of a cross section of the cross-linked body is shown in FIG. 11.

COMPARATIVE EXAMPLE 2

Figure 12:
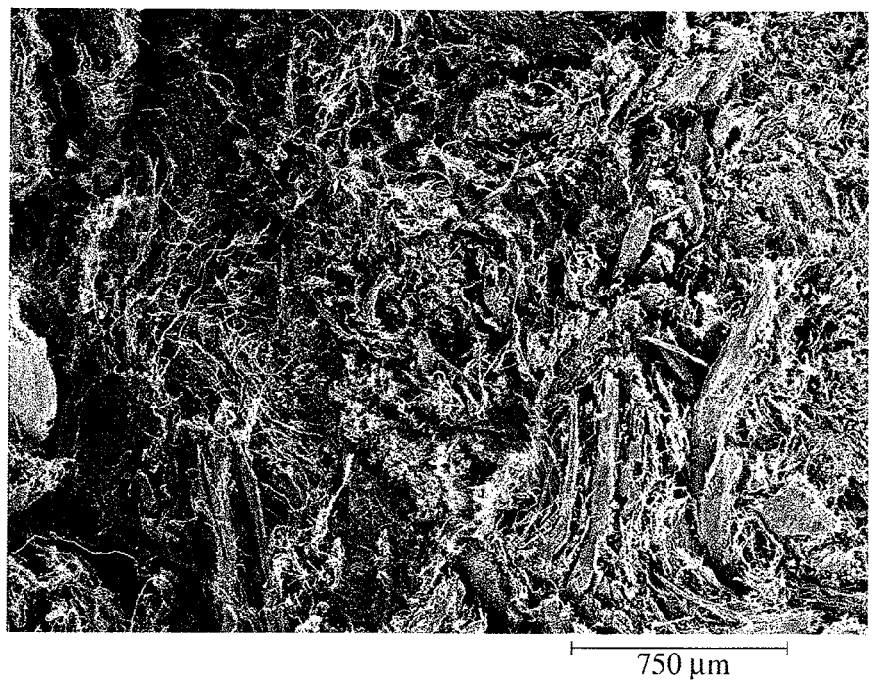
FIG. 12 is a scanning electron photomicrograph (SEM photograph) showing a cross section of the porous body of Comparative Example 2 comprising long apatite/collagen composite fibers.

A gel molding was produced in the same manner as in Examples 1-3, except that a dispersion containing long apatite/collagen composite fibers without short apatite/collagen composite fibers, compressed from above by a ball to measure the gel strength, and then subjected to the cross-linking of collagen. Because the gel molding had supernatant water, the gel strength was measured by compressing the gel molding by 5 mm from a position at which it was applied a force of 0.01 N after the ball came into contact with the molding surface. The measurement results are shown in FIG. 5 and Table 2. The SEM photograph of a cross section of the cross-linked body containing long apatite/collagen composite fibers is shown in FIG. 12. It is clear from FIG. 12 that the long apatite/collagen composite fibers were compacted, forming few pores.

REFERENCE EXAMPLE 1

Figure 13:
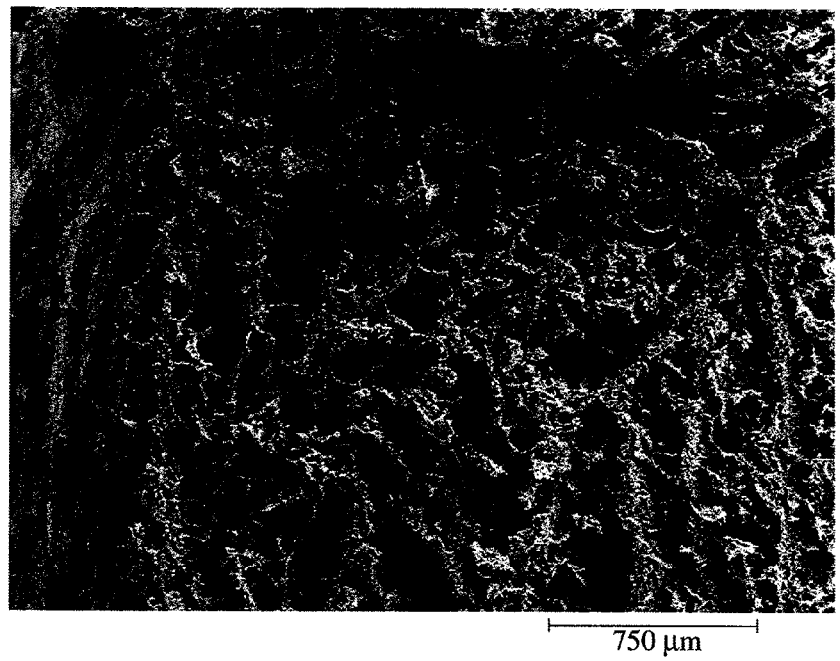
FIG. 13 is a scanning electron photomicrograph (SEM photograph) showing a cross section of the porous body of Reference Example 1 comprising short apatite/collagen composite fibers and a binder.

A gel molding was produced in the same manner as in Examples 1-3, except that 1 g of short apatite/collagen composite fibers, and 1 g of an aqueous phosphoric acid solution containing collagen as a binder (concentration: 0.97% by weight, and phosphoric acid: 20 mM) were stirred with 7.87 ml of PBS. After the strength of the gel molding was measured, collagen in the molding was cross-linked. The measured gel strength is shown in FIG. 5 and Table 2. The SEM photograph of the cross-linked body is shown in FIG. 13.

TABLE 1

| | Mass Ratio | |
|---|---|---|
| No. | Long Fibers | Short Fibers |
| Example 1 | 0.25 | 0.75 |
| Example 2 | 0.5 | 0.5 |

TABLE 1-continued

| No. | Mass Ratio | |
| --- | --- | --- |
| | Long Fibers | Short Fibers |
| Example 3 | 0.75 | 0.25 |
| Comparative Example 1 | 0 | 1 |
| Comparative Example 2 | 1 | 0 |
| Reference Example 1 | 0 | 1 |

TABLE 2

| No. | Load (N) |
| --- | --- |
| Example 1 | 0.14 |
| Example 2 | 0.12 |
| Example 3 | 0.14 |
| Comparative Example 1 | 0.06 |
| Comparative Example 2 | 1.35 |
| Reference Example 1 | 0.08 |

Figure 14:
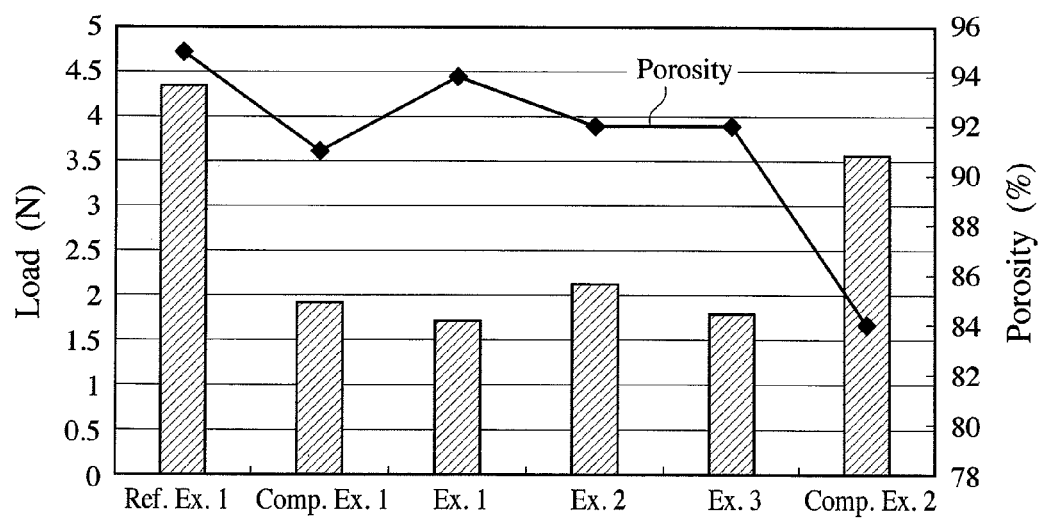
FIG. 14 is a graph showing the force necessary for compressing the porous bodies of Examples 1-3, Comparative Examples 1 and 2, and Reference Example 1, and their porosities.

The porous bodies of Examples 1-3, Comparative Examples 1 and 2, and Reference Example 1 were measured with respect to porosity and a force necessary for 3-mm compression. The measurement results are shown in FIG. 14 and Table 3.

TABLE 3

| No. | Force (N) | Porosity (%) |
| --- | --- | --- |
| Example 1 | 1.716 | 94 |
| Example 2 | 2.124 | 92 |
| Example 3 | 1.798 | 92 |
| Comparative Example 1 | 1.919 | 91 |
| Comparative Example 2 | 3.564 | 84 |
| Reference Example 1 | 4.347 | 95 |

If a force necessary for 3-mm compression is about 1.5 N, it may be said that a porous body has practically enough strength for bone fillers. It may thus be concluded that the apatite/collagen porous bodies of Examples 1-3 had sufficient mechanical strength. Also, the apatite/collagen porous bodies of Examples 1-3 had comparable porosities to the binder-containing porous body of Reference Example 1.

On the contrary, the porous body of Comparative Example 2 containing no short apatite/collagen composite fibers did not have large porosity. This appears to be due to the fact that long fibers were not well dispersed because no short fibers substantially acting as a binder were contained. In addition, without long apatite/collagen composite fibers as in Comparative Example 1, a gel molding having sufficient strength was not obtained, with extremely poor operability.

EFFECT OF THE INVENTION

In the method of the present invention for producing an apatite/collagen porous body, a slurry containing long fibers and short fibers both composed of an apatite/collagen composite is gelled, and then collagen is cross-linked. Mixing of long fibers with short fibers entangles the short fibers with the long fibers, contributing to the dispersion of the long fibers. Namely, the short fibers act like a binder in the slurry, a uniformly dispersed slurry can be obtained without adding a binder such as collagen, etc. The production method comprising uniformly dispersing the apatite/collagen composite fibers can produce a porous body having large porosity. Also, the gel and porous body comprising long fibers have excellent mechanical strength. Further, the apatite/collagen porous body comprising no binder has a high percentage of an apatite/collagen composite exposed to the surface, exhibiting large biodegradability.

Thus, the apatite/collagen composite fibers obtained by the production method of the present invention have good porosity and mechanical strength as well as excellent biocompatibility, thereby being suitable as biomaterials such as artificial bones, etc.

What is claimed is:

1. A method for producing a porous body comprising apatite/collagen composite fibers comprising:
    gelling a dispersion comprising long apatite/collagen composite fibers having an average length of 10-75 mm, wherein at least 90% by mass of the long apatite/collagen composite fibers has a length in the range of 5-100 mm, short apatite/collagen composite fibers having an average length of 0.05-1 mm, wherein at least 90% by mass of the short apatite/collagen composite fibers has a length in the range of 0.01-2 mm, and a liquid;
    freezing and drying the resultant gel to form a porous body; and
    cross-linking collagen in said porous body.

2. The method for producing a porous body comprising apatite/collagen composite fibers according to claim 1, wherein a binder is not added to said dispersion.

3. The method for producing a porous body comprising apatite/collagen composite fibers according to claim 1, wherein the ratio of said long fibers to said short fibers is 0.2-0.8 in said dispersion.

4. The method for producing a porous body comprising apatite/collagen composite fibers according to claim 2, wherein the ratio of said long fibers to said short fibers is 0.2-0.8 in said dispersion.

* * * * *